United States Patent [19]

Moeller et al.

[11] Patent Number: 4,668,705

[45] Date of Patent: May 26, 1987

[54] SEBOSUPPRESSIVE PREPARATIONS CONTAINING ALKOXYARYL ALKANOLS

[75] Inventors: Hinrich Moeller; Siegfried Wallat, both of Monheim, Fed. Rep. of Germany

[73] Assignee: Henkel Kommanditgesellschaft auf Aktien, Duesseldorf, Fed. Rep. of Germany

[21] Appl. No.: 645,945

[22] Filed: Aug. 30, 1984

[30] Foreign Application Priority Data

Sep. 9, 1983 [DE] Fed. Rep. of Germany ....... 3332505

[51] Int. Cl.[4] .......................................... A61K 31/075
[52] U.S. Cl. ..................................... 514/718; 514/864
[58] Field of Search .............................. 514/718, 864

[56] References Cited

U.S. PATENT DOCUMENTS

| 2,400,006 | 5/1946 | Jones et al. | 513/718 |
| 3,663,716 | 5/1972 | Stolar | 424/343 |
| 4,219,570 | 8/1980 | Inazuka et al. | 513/718 |
| 4,331,655 | 5/1982 | Tur | 424/59 |
| 4,435,605 | 3/1984 | Butts et al. | 568/878 |

FOREIGN PATENT DOCUMENTS 1569424  6/1980  United Kingdom.

OTHER PUBLICATIONS

Bettarini, Acaricide Compounds, CA 99:53342p (1983), p. 520.
Benzyl Alcohol etc., CA 100:174437w (1984), p. 596.

Primary Examiner—Jerome D. Goldberg
Assistant Examiner—F. Krosnick
Attorney, Agent, or Firm—Ernest G. Szoke; Henry E. Millson, Jr.; Mark A. Greenfield

[57] ABSTRACT

Substituted benzyl alcohols and substituted phenyl ethanols which are novel and the use of these and related compounds known per se, as sebosuppressives.

10 Claims, No Drawings

SEBOSUPPRESSIVE PREPARATIONS CONTAINING ALKOXYARYL ALKANOLS

BACKGROUND OF THE INVENTION

1. Field of the Invention

This invention relates to certain alkoxyaryl alkanols and their use in topical preparations for improving the oily and unaesthetic appearance of the hair, scalp and skin.

2. Statement of the Related Art

In modern cosmetology, efforts are constantly being made to reduce the oily, unaesthetic appearance of the hair, scalp and skin caused by excessive secretion of the sebaceous glands. Accordingly, frequent attempts have been made to normalize (i.e. reduce) the secretion of the sebaceous glands by suitable preparations in order to restore the hair and skin to its healthy appearance. Cosmetic preparations containing additions of sulfur, mercury or tar have been used to control seborrhea of the scalp. Unfortunately, it has been found that these known antiseborrheic additives frequently produce side effects after prolonged use, without giving really satisfactory results in regard to efficacy and performance properties. U.S. Pat. No. 4,331,655 and corresponding German Application No. 29 26 267 describe 3,7,11-trimethyl-2,6,10-dodecatrien-1-ol ethyl ether and/or acetate as additives to cosmetic preparations for normalizing the secretion of sebum. Unfortunately, it has been found that these compounds have only a very weak antiseborrheic effect. It is therefore highly desirable to provide a cosmetic preparation which has a stronger effect than corresponding known preparations without any adverse consequences on the human body.

DESCRIPTION OF THE INVENTION

It has now surprisingly been found that certain alkoxyaryl alkanols, some of which are novel, show outstanding antiseborrheic effects, even in very small doses.

Accordingly, the present invention relates to cosmetic preparations which are characterized by an effective sebosuppressive content of at least one alkoxyaryl alkanol corresponding to the following general formula, as well as to some of these alkoxyaryl alkanols per se:

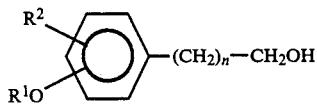

wherein
$R^1$ is a linear or branched $C_{4-20}$-alkyl and $R^1O$ occupies the 2, 3, or 4 (preferably 4) position on the ring;
$R^2$ is a $C_{1-4}$-alkyl, $C_{1-4}$-alkoxy, OH, or H (preferably H) and $R^2$ occupies a position on the ring other than $R^1$; and
n is 0 or 1.

Some of the compounds used in accordance with the invention are novel and all may be produced by generally known methods. One preferred process for their production is based on the catalytic or chemical reduction, (preferably using complex hydrides of aluminium or boron), of the correspondingly substituted arene carboxylic acid esters, arene carbaldehydes and aryl acetic acid esters or aryl acetaldehydes.

Another process is based on hydrolysis of the corresponding alkoxy aryl alkyl halides. In some cases, the direct alkylation of aromatic compounds with formaldehyde is also possible.

The benzyl alcohols or respective phenyl ethan-2-ols substituted at 2, 3, or 4 by the following groups are mentioned as examples of alkoxyaryl alkanols which may be used in accordance with the invention: butoxy-, tert.-butoxy-, hexyloxy-, heptyloxy-, octyloxy-, (2-ethyl-hexyloxy)-, nonyloxy-, isononyloxy-, (3,5,5-trimethyl-hexyloxy)-, decyloxy-, undecyloxy-, dodecyloxy-, isotridecyloxy-, tetradecyloxy-, (2-hexyldecyloxy)-, hexadecyloxy-, octadecyloxy-, eicosyloxy-, 4-dodecyloxy-3-methoxy, 4-dodecyloxy-3-hydroxy-, 4-tetradecyloxy-2-hydroxy-, 2-dodecyloxy-3-methyl-, 3-octyloxy-4-ethoxy-, or 2-decyloxy-4-methyl-; or 2-(4-decyloxyphenyl)-ethanol.

The compounds according to the invention show pronounced sebosuppressive activity combined with excellent compatibility with the skin and mucous membrane. They may be incorporated without difficulty in various cosmetic preparations, such as aqueous or alcoholic solutions, oils, suspensions, gels, emulsions, salves or aerosols. For treating seborrheic skin and oily hair, these preparations may be applied in any of the usual forms, such as hair lotions, shampoos, hair treatment agents, hair rinses, skin lotions or shaking mixtures. They are preferably used in a hair care preparations. In addition to the active substance combination according to the invention, these cosmetic preparations may contain standard auxiliaries and vehicles, such as water, organic solvents, surfactants, emulsifiers, oils, fats, waxes, fragrances, dyes, preservatives and the like. The new sebosuppressive compositions contain about from 0.01 to 5.0% by weight and preferably about from 0.05 to 1.0% by weight of the alkoxyaryl alkanols. Unless otherwise indicated, all percentages are by weight based upon the total weight of the composition.

PRODUCTION EXAMPLES (A) 4-tetradecyloxybenzyl alcohol (new compound)

1.35 g (36 mMols) of sodium borohydride and then 3.1 g (36 mMols) of lithium bromide were stirred into 60 ml of diethylene glycol dimethyl ether. After stirring for 30 minutes, 20.0 g (57 mMols) of 4-tetradecyloxybenzoic acid methyl ester were added. The mixture was heated for 3.5 hours to 100° C. and poured in portions onto a mixture of 500 g of ice and 50 ml of concentrated hydrochloric acid, after which the deposit formed was filtered off and stirred with a little methylene chloride. The undissolved fraction was then filtered off and recrystallized from n-hexane. 4-tetradecyloxybenzyl alcohol melting at 73° to 75° C. was obtained in a yield of 12.5 g.

(B) 4-decyloxybenzyl alcohol was obtained in the same way as (A): M.p. 55°–57° C.

(C) 2-(4-decyloxyphenyl)-ethanol (new compound)

was obtained from 2-(4-decyloxyphenyl)-acetic acid methyl ester by the procedure adopted for (A): M.p. 42°–44° C.

(D) 4-dodecyloxybenzyl alcohol (new compound)

was obtained in the same way as (A): M.p. 65°–66° C.

(E) 4-hexyloxybenzyl alcohol was obtained in the same way as (A): M.p. 32°–33° C.

(F) 4-octyloxybenzyl alcohol was obtained in the same way as (A): M.p. 47°–48° C.

(G) 2-decyloxybenzyl alcohol was obtained in the same way as (A): B.p. 153°–156° C./0.04 mbar.

(H) 3-dodecyloxybenzyl alcohol (new compound)

was obtained in the same way as (A): 44°–46° C.

(I) 3-tetradecyloxybenzyl alcohol (new compound)

was obtained in the same way as (A): M.p. 50°–53° C.

(J) 2-dodecyloxybenzyl alcohol was obtained in the same way as (A): B.p. 166° C./0.03 mbar
n: 1.4968

(K) 3-decyloxybenzyl alcohol (new compound)

was obtained in the same way as (A): M.p. 37°–39° C.

(L) 4-octadecyloxybenzyl alcohol (new compound)

was obtained in the same way as (A): M.p. 84°–87° C.

(M) 4-(2-ethylhexyloxy)-benzyl alcohol (new compound)

was obtained in the same way as (A): B.p. 130° C./0.15 mbar.
n: 1.5068

(N) 4-(3,5,5-trimethylhexyloxy)-benzyl alcohol (new compound)

was obtained in the same way as (A): n: 1.5025

(O) 4-(2-hexyldecyloxy)-benzyl alcohol (new compound)

was produced in the same way as (A): n: 1.4932

(P) 4-dodecyloxy-3-methoxybenzyl alcohol (new compound)

was obtained in the same way as (A): M.p. 55°–57° C.

The antiseborrheic effect was closely studied using the animal tests described in the following:

The test animals were male Wistar rats having a body weight of 220 to 230 g at the beginning of the tests. The degree of browning on the shaved back of the rats was visually assessed. Browning is produced by the brown skin surface lipid of the rats. This test is based on the observation that young male and female rats washed with surfactant solution or with a lipid solvent and also male rats systematically treated with oestrogen only have the normal light, pink-colored skin after shaving. At the same time, only comparatively very small quantities of lipids can be extracted from the shaved hairs.

In order to assess effectiveness, the test substances in solution in alcohol were each brushed onto half the back of 6 rats. The other half was only treated with the solvent minus active substances.

Over the test period of 14 days, the test substances were applied once daily for a total of 9 days. A group of 6 rats which remained completely untreated was used for further control. At the end of the test, the animals were shaved on their back and sides and were visually assessed independently by an examination panel of 6 people under double blind conditions.

Evaluation methods

The first criterion evaluated was whether the majority of examiners correctly recognized the treated side, differentiation being carried out as follows:

| Symbol | Percentage of examiners noticing an effect |
|---|---|
| ++ | 100% |
| + | >50%–100% |
| 0 | ≦50% |

The second criterion evaluated was the difference between the righthand side and the lefthand side, each examiner having to award 1 point per animal on the following basis:
 darker side—1 point
 lighter side—0 point and
 both sides the same—0.5 point Significant differences between the untreated and treated sides in the second method of evaluation indicate the local effectiveness of a substance.

The third criterion evaluated was the difference in intensity between the shades of brown using the following scale:
 3 points—dark brown
 2 points—medium brown
 1 point—light brown
 0 points—no browning In the third method of evaluation, total point differences are compared between the untreated control animals and the treated and untreated sides of the test animals, significant differences between the control animals and the treated side of the test animals again indicating the effectiveness of a substance.

There is generally also a distinct difference between the untreated and treated sides of the same test animals. However, this difference is not always as clear as that between the control animals and the treated sides, for which there may be various reasons, such as mechanical transfer of substance from one side to the other or solvent influence.

The following scheme was used for differentiating the effects according to evaluation methods 2 and 3:

| Symbol | Points difference |
|---|---|
| ++ | very large (≧99.9% probability) |
| + | significant (≧95% probability) |
| 0 | minimal (95% probability) |

Percentage sebum reduction

The sebum reduction is calculated from the points difference by working out the quotient between the points difference $\Delta P$ and the number of points for the control group $P_k$, and expressing the value obtained in percent.

Sebum reduction = $(\Delta P/P_k \cdot 100$ [%]

The p-alkoxybenzoic acid esters of the inventive compounds were applied in the manner described in concentrations of 0.1%, 0.2% and 1.0% in alcohol/acetone (1:1). The results are given in the following Table.

TABLE

Evaluation of sebosuppressive effects

| Compound | Conc. (%) | Evaluation method 1 | 2 | 3 | Sebum reduction (%) |
|---|---|---|---|---|---|
| A | 0.5 | ++ | ++ | ++ | 97 |
| B | 0.2 | ++ | ++ | ++ | 95 |
| C | 1.0 | ++ | ++ | ++ | 56 |
| D | 0.1 | ++ | ++ | ++ | 88 |
| E | 0.2 | ++ | ++ | ++ | 92 |
| F | 0.2 | ++ | ++ | ++ | 95 |
| G | 0.5 | ++ | ++ | ++ | 20 |
| H | 0.5 | ++ | ++ | ++ | 69 |
| I | 0.5 | ++ | ++ | ++ | 22 |
| K | 0.5 | ++ | ++ | ++ | 53 |
| Benzyl alcohol (according to U.S. Pat. No. 3,663,716) | 1.0 | 0 | 0 | 0 | 0 |

Although any suppression of sebum production is useful for the purposes of this invention, a reduction of at least 50% (compounds A, B, C, D, E, F, H and K) is preferred, a reduction of at least 75% (compounds A, B, D, E and F) is more preferred, and a reduction of at least 90% (compounds A, B, E and F) is most preferred.

Examples of cosmetic formulations

Formulations for topical preparations according to the invention for the treatment of very oily hair and seborrheic skin are given in the following:

| | Parts by weight |
|---|---|
| 1. Shampoo for oily hair | |
| Ammonium lauryl sulfate containing 33–35% of wash-active (Texapon A) | 40.0 |
| Coconut oil fatty acid diethanolamide | 3.0 |
| Sodium chloride | 2.0 |
| Sodium sulfate | 2.0 |
| 4-dodecyloxybenzyl alcohol (INVENTION COMPOUND D) | 0.5 |
| Preservative | 0.1 |
| Perfume oil | 0.1 |
| Water | 52.3 |
| 2. Hair treatment | |
| Glycerol mono-distearate (Tegin M) | 0.7 |
| Cetyltrimethyl-ammonium chloride cationic surfactant (Dehyquart A) | 2.0 |
| Cholesterol | 0.2 |
| Soya lecithin | 0.3 |
| Mixture of cetylstearyl alcohol with nonionic emulsifiers (Emulgade A) | 8.0 |
| Perfume oil | 0.3 |
| 4-decyloxybenzyl alcohol (INVENTION COMPOUND B) | 0.2 |
| Water, fully deionized | 88.3 |
| 3. Skin cream | |
| Self-emulsifying mixture of mono/diglycerides of higher saturated fatty acids with potassium stearate (Cutina KD 16) | 16.0 |
| Cetyl stearyl alcohol containing approximately 12 mols of ethylene oxide (Emulgin B 1) | 1.0 |
| 2-octyl dodecanol | 8.0 |
| Isopropyl myristate | 6.0 |
| Glycerol | 6.0 |
| 4-octyloxybenzyl alcohol (INVENTION COMPOUND F) | 0.5 |
| Water | 62.5 |

Suppliers of trademarked products mentioned:
Texapon A=Henkel KGaA, Germany
Comperlan KD=Henkel KGaA
Cutina KD 16=Henkel KGaA
Emulgade A=Henkel KGaA
Eumulgin B 1=Henkel KGaA
Tegin M=Atlas Chemie, Germany
Dehyquart A=Henkel KGaA The foregoing formulations are conventional except for the inclusion of the inventive sebosuppressive compound. The nature and amount of the sebosuppressive compound need not vary, regardless of whether the formulations are for shampoos, hair treating agents, or skin creams. All formulations, regardless of use, are preferably water-based. Shampoos, cleansing creams, etc., should contain at least one surfactant. Skin creams should contain emollients such as mono- or di-glycerides of saturated higher fatty acids, preferably with a suitable emulsifier.

It is also possible for the sebosuppressive compound of this invention to be used in a pharmaceutical manner, when applied in a pharmaceutically effective sebosuppressive amount, and in a suitable carrier or adjuvant.

The method of treating seborrheic skin, scalp or hair conditions using the inventive compositions is to apply each formulation in the same manner it would be applied if it were not sebosuppressive.

We claim:

1. A method for treating seborrheic skin or hair comprising the topical application to said seborrheic skin or hair of a composition containing a sebosuppressive-effective amount of the compound of the formula

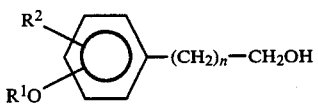

wherein
$R^1$ is linear or branched $C_{4-20}$-alkyl and $R^1O$ occupies the 2, 3, or 4 position on the ring;
$R^2$ is $C_{1-4}$-alkyl, $C_{1-4}$-alkoxy, OH, or H and $R^2$ occupies a position on the ring other than $R^1$ and
n is 0 or 1.

2. The method of claim 1 wherein $R^1O$ occupies the 4 position.

3. The method of claim 1 wherein $R^2$ is H.

4. The method of claim 2 wherein $R^2$ is H.

5. The method of claim 1 wherein said compound is
a benzyl alcohol or phenyl-ethan-2-ol substituted at the 2, 3, or 4 ring position by: butoxy; hexyloxy; heptyloxy; octyloxy; (2-ethylhexyloxy); nonyloxy; isononyloxy; (3,5,5-trimethyl-hexyloxy); decyloxy; undecyloxy; docecyloxy; isotridecyloxy; tetradecyloxy; (2-hexyldecyloxy); hexadecyloxy; octadecyloxy; eicosyloxy;
a benzyl alcohol or phenyl-ethan-2-ol substituted at the 2, 3, or 4 ring position by:
4-docecyloxy-3-methoxy; 4-dodecyloxy-3-hydroxy;
4-tetradecyloxy-2-hydroxy; 2-dodecyloxy-3-methyl;
3-octyloxy-4-ethoxy; 2-decyloxy-4-methyl; or
2-(4-decyloxyphenyl)-ethanol.

6. The method of claim 1 wherein said compound is:
4-tetradecyloxybenzyl alcohol;
4-decyloxybenzyl alcohol;
2-(4-decyloxyphenyl)-ethanol;
4-dodecyloxybenzyl alcohol;
4-hexyloxybenzyl alcohol;

4-octyloxybenzyl alcohol;
2-decyloxybenzyl alcohol;
3-dodecyloxybenzyl alcohol;
3-tetradecyloxybenzyl alcohol;
2-dodecyloxybenzyl alcohol;
3-decyloxybenzyl alcohol;
4-octodecyloxybenzyl alcohol;
4-(2-ethylhexyloxy)-benzyl alcohol;
4-(3,5,5-trimethylhexyloxy)-benzyl alcohol;
4-(2-hexyldecyloxy)-benzyl alcohol; or
4-dodecyloxy-3-methoxybenzyl alcohol.

7. The method of claim 1 wherein said compound is present in about 0.01 to 5.0% by weight, based upon the total weight of the composition.

8. The method of claim 1 wherein said compound is present in about 0.05 to 1% by weight, based upon the total weight of the composition.

9. The method of claim 6 wherein said compound is present in about 0.01 to 5.0% by weight, based upon the total weight of the composition.

10. The method of claim 6 wherein said compound is present in about 0.05 to 1% by weight, based upon the total weight of the composition.

* * * * *